(12) United States Patent
Benner

(10) Patent No.: US 11,708,389 B1
(45) Date of Patent: Jul. 25, 2023

(54) INFORMATION STORAGE WITH RECTIFIED DNA

(71) Applicant: Steven Benner, Gainesville, FL (US)

(72) Inventor: Steven Benner, Gainesville, FL (US)

(*) Notice: Subject to any disclaimer, the term of this patent is extended or adjusted under 35 U.S.C. 154(b) by 978 days.

(21) Appl. No.: 16/450,941

(22) Filed: Jun. 24, 2019

Related U.S. Application Data

(60) Provisional application No. 62/688,454, filed on Jun. 22, 2018.

(51) Int. Cl.
  *C07H 19/20* (2006.01)
  *C07H 19/10* (2006.01)
  *C07H 19/23* (2006.01)

(52) U.S. Cl.
  CPC .............. *C07H 19/10* (2013.01); *C07H 19/23* (2013.01)

(58) Field of Classification Search
  CPC ....... C12P 17/165; C12P 19/34; C12N 9/1252; C12N 15/11; C07H 19/20; C07H 15/252
  USPC ............................................. 536/23.2
  See application file for complete search history.

(56) References Cited

OTHER PUBLICATIONS

Havermann et al., Nucl, Nucll, Nucl acid, 2008, 27(30) abstract.*
Lutz et al. Nucleic acid Research, 2004, 32, pp 728-735.*

* cited by examiner

*Primary Examiner* — Robert B Mondesi
*Assistant Examiner* — Mohammad Y Meah

(57) ABSTRACT

Disclosed here are compositions of matter that comprise DNA analogues that have been rectified by replacing the four standard components with alternative components that mitigate various problems frequently encountered during synthesis of these compounds, during the functioning of these compounds, and complex mixtures for information data storage.

1 Claim, 3 Drawing Sheets

INFORMATION STORAGE WITH RECTIFIED DNA

CROSS REFERENCE TO RELATED APPLICATIONS:

This application claims priority to U.S. Provisional Pat. Application 62688454, entitled " Information Storage with Rectified DNA ".

BACKGROUND OF THE INVENTION

1. Field of the Invention

This invention relates to analogs of DNA and RNA of various types, including analogs that are more suited for use in non-genetic processes, including the storage of information, as tags for combinatorial synthesis, and in molecular computing.

2. Description of Related Art

In the current art, synthetic DNA is principally used as a genetic molecule in a biological context. This includes long DNA molecules that are assembled from chemically and/or enzymatically synthesized fragments, possibly to serve as genes that are transcribed to give RNA molecules that encode proteins, are incorporated into the chromosomes of living cells, or to support biotechnology. Shorter DNA fragment find use as primers, probes, and in countless other applications on which modern biotechnology is based.

However, synthetic DNA has values other than in these genetic roles within a biological system. Synthetic DNA and its analogs have been offered for many "non-biological" applications. Some of those known in the art are recited below:

1. As a tag in combinatorial diversity synthesis. For example, quarter of a century ago, Lerner, Brenner and others proposed to use co-synthesized DNA molecules to record the history of chemical reactions as they were applied to synthesize components of libraries of molecules [Brenner, S., Lerner, R. A. (1992). Encoded combinatorial chemistry. *Proc. Natl. Acad. Sci. USA* 89, 5381-5383.]. This co-synthesis might be done on a bead or within a reaction compartment, where a reaction to add units to a library of molecules is followed by addition of one or more nucleotides. Illustrating in a split and pool architecture on beads, after a particular chemical reaction is applied to intermediates attached to the beads in a multistep synthesis, that reaction is recorded on that bead by adding by synthesis a DNA fragment that encodes the reaction.

2. For information storage. The art presently shows considerable interest in using molecular systems built from a vocabulary of building blocks to store information [Grass, R. N., Heckel, R., Puddu, M., Paunescu, D., Stark, W. J. (2015). Robust chemical preservation of digital information on DNA in silica with error-correcting codes. *Angew. Chem. Int. Ed.* 54, 2552-2555]. Molecular information storage may provide higher information density, bits stored per unit volume. While proteins and non-biological polymers have been suggested as molecular information storage systems, DNA is the primary polymer considered for this purpose. Various ways have been proposed to encode information in DNA molecules, and some hope that advances in DNA synthesis platforms and DNA sequencing platforms will all petabytes of information to be stored in synthetic DNA in a way that can be retrieved.

3. For molecular computing. A quarter century ago, Adleman proposed that the high information density of DNA mixtures could be used for highly parallel molecular computing [Adleman, L. (1994) Molecular computation of solutions to combinatorial problems. *Science* 266, 1021-1029.]. Multiple examples of this have emerged [Reif, J. H., & LaBean, T. H. (2007, July). Autonomous programmable biomolecular devices using self-assembled DNA nanostructures. *In International Workshop on Logic, Language, Information, and Computation.* pp. 297-306. Springer, Berlin][Ahrabian, H., Nowzari-Dalini, A. (2004). DNA simulation of nand Boolean circuits. *Advanced Modeling and Optimization* 6, 33-39].

Unfortunately, DNA as it naturally occurs has intrinsic chemical properties that make it poorly suited for many of these functions. For example, the glycosidic bond that joins the nucleobase to the 2'-deoxyribose ring is well known to be sensitive to acid-catalyzed cleavage. Thus, when technologists wish to use DNA to encode tags during combinatorial synthesis, that synthesis process cannot include acid-catalyzed chemistry.

BRIEF SUMMARY OF THE INVENTION

The instant invention replaces nucleobases that are sensitive to acid-catalyzed cleavage to those that are stable to acid-catalyzed cleavage

DETAILED DESCRIPTION OF THE INVENTION

Figure 1:
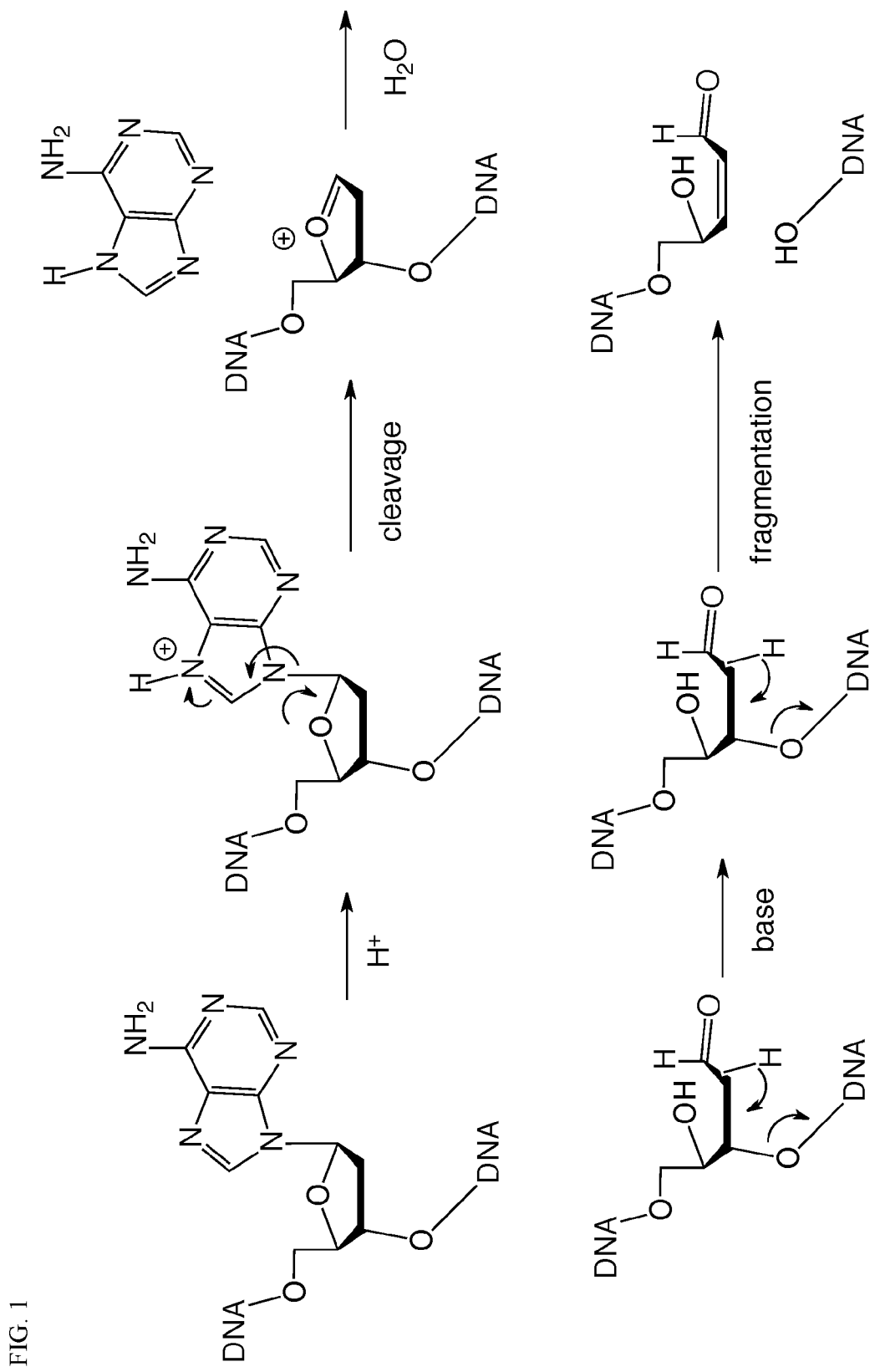
FIG. 1. Acid-catalyzed cleavage of the glycosidic bond in an exemplary nucleotide building block of DNA, 2'-deoxyadenosine. While not wishing to be bound by theory, a mechanism is proposed that involves protonation by the acid on the N-7 nitrogen of the nucleobase. Analogous cleavage processes are available to 2'-deoxyguanosine. Lost of the nucleobase can be followed by fragmentation of the DNA chain, as shown.

The vintage of some of these references and the very few examples where DNA has been used for non-biological applications suggest that obstacles must obstruct these concepts in practice. This disclosure teaches problematic limitations of natural DNA for these and other concept applications. Then, the instant inventions that are disclosed here provide compositions of matter assembled from a plurality of nucleotide analogs that mitigate those problematic limitations.

One set of problematic limitations relates to the chemical synthesis of DNA for genetic and non-genetic applications. Here, "chemical synthesis" refers to phosphoramidite, phosphotriester, or other processes that make DNA without involving enzymes in the nucleotide coupling steps. Chemical synthesis of DNA creates oligonucleotides contaminated with defective molecules. These defects, known in the art, are illustrated here for DNA, recognizing that similar issues apply to RNA and various of its sugar modified backbones, including (without limitation) species such as locked DNA, bicyclic DNA, RNA, and 2'-fluoro-2'-deoxy DNA, among others. In this application, "DNA" is understood to include these and other analogs.

The instant invention teaches that these particular problematic limitations can be usefully mitigated or resolved by changing the structure of the nucleotides, but in a way that allows them to continue to interface with standard enzymes, proteins, and nucleic acids in their natural or mutated forms. Speaking generally, the instant invention discloses replacements for adenine, guanine, cytosine, and thymine, and their analogs, that do not suffer from, or suffer less from, these problematic molecular features intrinsic to natural nucleoside building blocks, but still allow them to form nucleobase pairs with their complements (respectively) thymine and uracil, cytosine, guanine, and adenine. These are referred to as "conversion attribute."

At a minimum, to have the attribute, oligonucleotides containing the replacements for adenine, guanine, cytosine, thymine, and their analogs must, immediately or eventually, pair with complementary oligonucleotides in simple strand-strand hybridization procedures. Further, that pairing must have the same specificity as the pairing with fully natural oligonucleotides (recognizing that even totally natural nucleobase pairing is not perfectly specific). This is one example of a "conversion attribute"

Further value is gained if the replacements for adenine, guanine, cytosine, and thymine, and their analog nucleobases interact with their complements with the same specificity as their natural components in the active sites of DNA polymerases, RNA polymerases, reverse transcriptases, or other enzymes charged with replicating oligonucleotides. This is another example of a "conversion attribute".

Still further value is gained if the replacements for adenine, guanine, cytosine, and thymine, and their analogs, assembled by chemical synthesis into an oligonucleotide of the instant invention, lead to the production of another oligonucleotide (or oligonucleotides) that is (are) either fully natural, or sufficiently natural to be used in living systems, including living cells. As an example without limit, to have fully conversion attributes, oligonucleotides of the instant invention must be able to template a polymerase chain reaction (PCR) that generates multiple copies of a natural DNA that substantially preserves the information in the oligonucleotide(s) of the instant invention. This is another example of a "conversion attribute".

The problematic limitations of standard DNA (and, by analogy, RNA and other analogs) are now summarized individually, together with the instant inventions taught by this specification to mitigate them.

One set of limitations relates to the chemical synthesis of DNA, where "chemical synthesis" reflects phosphoramidite, phosphotriester, or other systems that do not involve enzymes. Chemical synthesis of DNA always creates oligonucleotides contaminated with defective molecules, with only the amounts of those defective oligonucleotides depending on the precise process by which those oligonucleotides were prepare. These defects, known in the art, are illustrated here for DNA, recognizing that similar issues apply to RNA and various of its sugar modified backbones, including (without limitation) species such as locked DNA, bicyclic DNA, RNA, and 2'-fluoro-2'-deoxy DNA. We teach some of them individually.

The glycosyl bond attaching the nucleobase to the 2'-deoxy ribose unit in the backbone is easily cleaved under acidic conditions. This is especially problematic in standard phosphoramidite-based chemical synthesis, where acidic conditions are repeatedly applied to remove trityl protecting groups in growing DNA strands. This leads to product oligocleotides that are defective in that they have lost a nucleobase at one or more sites. This loss generally leads to the fragmentation of the oligonucleotide.

The standard nucleobases of standard DNA can react under the alkaline conditions used to protect the nucleobases during chemical synthesis. For example, cytosine is readily deaminated to give uracil, changing the information content of the synthetic DNA oligonucleotide. Adenine may be deaminated to inosine, which pairs best with cytosine in a duplex, also changing the information content of the synthetic DNA.

Figure 2:
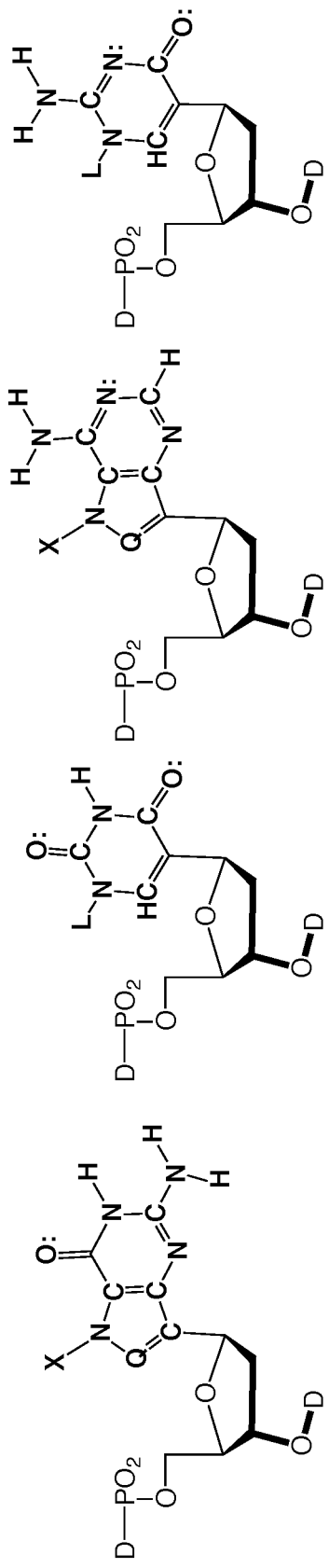
FIG. 2. Compositions of the instant invention that mitigate the undesired acid-catalyzed reactivity of standard 2'-deoxyribonucleotides. These are deoxyribonucleotides that comprise at least 10 nucleotides, wherein two or more of said nucleotides are replaced by a 2'-deoxyribonucleotide analog having a D-configuration selected from structures shown, wherein D is the point of attachment of said analog to the preceding and following nucleotides in the deoxyribonucleotide, X and L are side chains that are independently selected to be methyl, lower alkyl, functionalized alkyl, such as carboxymethyl, and Q is either N or CH.

C-glycosides manage these by assembling an oligonucleotide of the instant invention from building blocks that replace some, most, or all of their adenine, guanine, cytosine, and thymine-containing building blocks. In natural DNA, each of these building blocks has its heterocycle joined to the oligonucleotide backbone by a carbon-nitrogen bond. In the claimed oligonucleotides of the instant invention, building blocks are analogs that have their heterocycles joined to the oligonucleotide backbone by a carbon-carbon bond. These are called "C glycosides". Representative structures are shown in FIG. 2.

This specification further teaches specific attachments for the heterocycles in these building blocks, the X and L groups in the Figures. These can either be more hydrophobic (for example, without limitation, methyl or ethyl) or more hydrophilic (for example, without limitation, carboxamidomethyl or hydroxyethyl), depending on the needs to mitigate other problematic limitations of DNA, as disclosed further below. However

EXAMPLES

Figure 3:
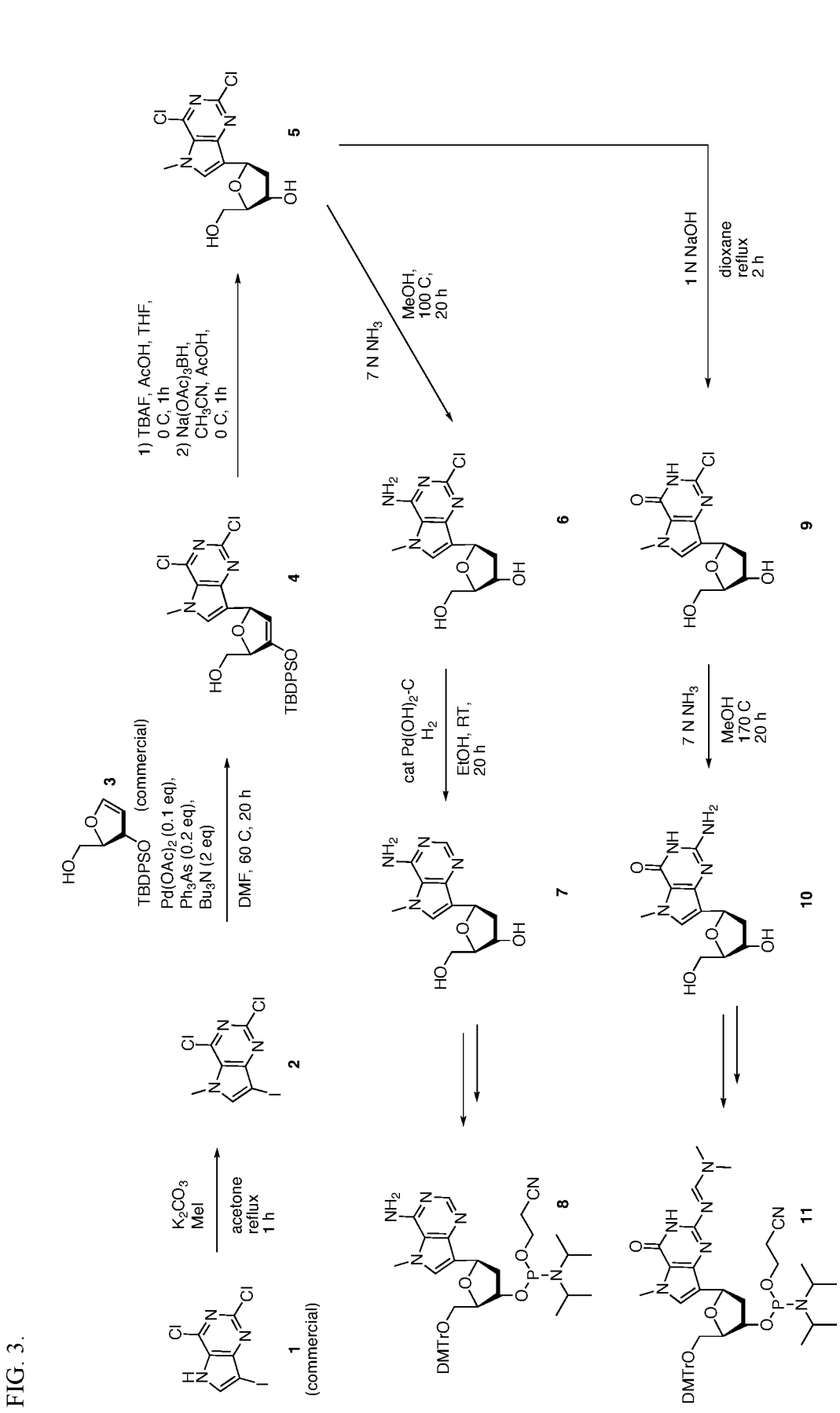
FIG. 3. Synthesis of one of the compositions of the instant invention that mitigate the undesired acid-catalyzed reactivity of standard 2'-deoxyribonucleotides.

Example 1. Synthesis of the 7-Me-A/G Analogs (FIG. 3)

Compound 2

Compound 1 (1.55 g, 5 mmol) is dissolved in acetone (50 mL). Potassium carbonate (690 mg, 5 mmol) is added, followed by iodomethane (1.5 mL, 25 mmol). The resulting suspension is heated under reflux for 1 h. The volatiles are removed in vacuo and the residue is partitioned between ethyl acetate (EtOAc) and saturated aqueous $NaHCO_3$ solution. The organic phase is dried ($Na_2SO_4$) and concentrated. The residue is purified by flash liquid chromatography on silica (FLC) to give compound 2.

Compound 4

A suspension of palladium acetate (34 mg, 0.15 mmol) and triphenyl arsine (92 mg, 0.3 mmol) in N,N-dimethylformamide (DMF) (6 mL) is stirred at room temperature for 30 minutes. To this is added a solution of compound 2 (328 mg, 1 mmol), compound 3 (430 mg, 1.2 mmol) and tributylamine (0.475 mL, 2 mmol) in DMF (8 mL). The resulting suspension is stirred at 60° C. for 20 h. The solids are centrifuged off (10,000 rpm, 5 min) and the supernatant is partitioned between EtOAC and saturated aqueous $NaHCO_3$ solution. The organic phase is dried ($Na_2SO_4$) and concentrated. The residue is purified by FLC to give compound 4.

Compound 5

A solution of compound 4 (555 mg, 1 mmol) and acetic acid (glac., 0.30 mL, 5 mmol) in THF (10 mL) is cooled to 0° C. A solution of tetrabutylammonium fluoride in THF (1 M, 1.5 mL, 1.5 mmol) is added. After 1 h at 0° C. the reaction is concentrated in vacuo. The residue is dissolved in acetonitrile (8 mL) and acetic acid (glac., 4 mL). The solution is cooled to 0° C., and sodium triacetoxyborohydride (254 mg, 1.2 mmol) is added. After stirring at 0° C. for 1 h the reaction is quenched by the addition of acetone (0.5 mL). The solution is concentrated and the residue purified by FLC to give compound 5.

Compound 6

Compound 5 (318 mg, 1 mmol) is dissolved in methanolic ammonia (7 N, 10 mL, 70 mmol). The solution is heated in a pressure vessel at 100° C. for 20 h. The volatiles are removed in vacuo and the residue is purified by FLC to give compound 6.

Compound 7

To a solution of compound 6 (149 mg, 0.5 mmol) in ethanol (20 mL) is added palladium hydroxide on carbon (20 wt% Pd, 50 mg, 0.1 mmol). The mixture is saturated with hydrogen and stirred under a hydrogen atmosphere (1 bar) at room temperature. After 20 h, the mixture is filtered over Celite, the volatiles are removed in vacuo, and the residue is purified by FLC to give compound 7.

Compound 8

Compound 8 is prepared from compound 7 following standard procedures for the preparation of nucleoside phosphoramidites:
A solution of compound 7 (264 mg, 1 mmol), 4,4'-dimethoxytrityl chloride (407 mg, 1.2 mmol) and 4-(dimethylamino)pyridine (12 mg, 0.1 mmol) in pyridine (10 mL) is stirred at room temperature for 4 h. The reaction is quenched by the addition of methanol (0.5 mL). The volatiles are removed in vacuo and the residue is purified by FLC.
This intermediate (454 mg, 0.8 mmol) is dissolved in dichloromethane (8 mL), and N,N-diisopropylethylamine (0.28 mL, 1.6 mmol) is added. The solution is cooled to 0° C. and 2-cyanoethyl N,N-diisopropylchlorophosphoramidite (0.22 mL, 1 mmol) is added. After 30 min at 0° C. the reaction is quenched by the addition of methanol (0.5 mL). The volatiles are removed in vacuo and the residue is purified by FLC to give compound 8.

Compound 9

A solution of compound 5 (318 mg, 1 mmol) in dioxane (10 mL) and aqueous sodium hydroxide solution (1 N, 2 mL, 2 mmol) is heated under reflux for 2 h. After concentration in vacuo, the residue is partitioned between EtOAc and saturated aqueous NaHCO$_3$ solution. The organic phase is dried (Na$_2$SO$_4$) and concentrated. The residue is purified by FLC to give compound 9.

Compound 10

Compound 9 (300 mg, 1 mmol) is dissolved in methanolic ammonia (7 N, 10 mL, 70 mmol). The solution is heated in a pressure vessel at 170° C. for 20 h. The volatiles are removed in vacuo and the residue is purified by FLC to give compound 10.

Compound 11

Compound 11 is prepared from compound 10 following standard procedures for the preparation of nucleoside phosphoramidites:
A solution of compound 10 (420 mg, 1.5 mmol) and N,N-dimethylformamide dimethyl acetal (1.33 mL, 10 mmol) in methanol (10 mL) is heated under reflux for 2 h. The volatiles are removed in vacuo and the residue is purified by FLC.

A solution of this intermediate (335 mg, 1 mmol), 4,4'-dimethoxytrityl chloride (407 mg, 1.2 mmol) and 4-(dimethylamino)pyridine (12 mg, 0.1 mmol) in pyridine (10 mL) is stirred at room temperature for 4 h. The reaction is quenched by the addition of methanol (0.5 mL). The volatiles are removed in vacuo and the residue is purified by FLC.
This intermediate (510 mg, 0.8 mmol) is dissolved in dichloromethane (8 mL), and N,N-diisopropylethylamine (0.28 mL, 1.6 mmol) is added. The solution is cooled to 0° C. and 2-cyanoethyl N,N-diisopropylchlorophosphoramidite (0.22 mL, 1 mmol) is added. After 30 min at 0° C. the reaction is quenched by the addition of methanol (0.5 mL). The volatiles are removed in vacuo and the residue is purified by FLC to give compound 11.

What is claimed is:
1. A polydeoxyribonucleotide comprising at least 10 nucleotide units, wherein two or more of said nucleotide units are replaced by a 2'-deoxyribonucleotide analog having a D-configuration selected from the group consisting of

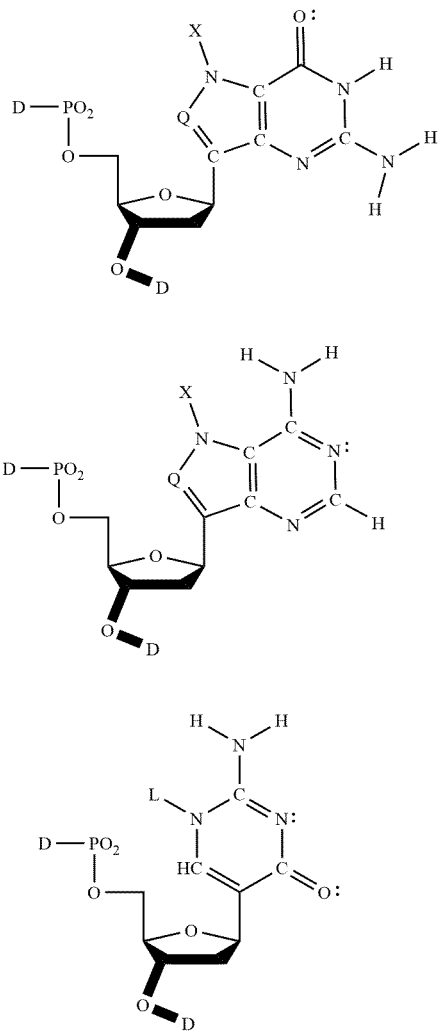

wherein D is the point of attachment of said analog to nucleotides in the polydeoxyribonucleotide, X and L are side chains that are independently selected to be alkyl, and Q is either N or CH.

* * * * *